United States Patent [19]

Bonnet et al.

[11] Patent Number: 5,137,948
[45] Date of Patent: Aug. 11, 1992

[54] PREPARATION OF FLAME-RESISTANT HALOGENATED IMIDES

[75] Inventors: Evelyne Bonnet, Lamorlaye; Andre Gagnieur, Rochetaille sur Saone; Bernard Gurtner, Grenoble, all of France

[73] Assignee: Atochem, Courbevoie, France

[21] Appl. No.: 224,207

[22] Filed: Jul. 22, 1988

Related U.S. Application Data

[63] Continuation-in-part of Ser. No. 11,099, Feb. 5, 1987, abandoned.

[30] Foreign Application Priority Data

Feb. 12, 1987 [FR] France .................... 86 01917
Jul. 24, 1987 [FR] France .................... 87 10586

[51] Int. Cl.$^5$ .................................... C07D 209/52
[52] U.S. Cl. .................................... 524/90; 524/94; 252/609; 548/451; 548/461; 548/473
[58] Field of Search .................... 252/609; 524/90, 94; 548/451, 461, 473

[56] References Cited

U.S. PATENT DOCUMENTS

| | | | |
|---|---|---|---|
| 2,420,702 | 5/1947 | Drewitt | 548/473 |
| 3,382,254 | 5/1968 | Jenkner et al. | 549/246 |
| 3,705,127 | 5/1972 | Cyba | 260/881 |
| 3,734,925 | 5/1973 | Minieri | 548/475 |
| 3,798,327 | 3/1974 | Minieri | 514/417 |
| 3,873,567 | 3/1975 | Cyba | 260/326 C |
| 4,087,441 | 5/1978 | Lee | 548/462 |
| 4,464,240 | 8/1984 | Hansen | 204/159.2 |
| 4,465,571 | 8/1984 | Hansen | 204/159.2 |

FOREIGN PATENT DOCUMENTS

| | | |
|---|---|---|
| 0101785 | 3/1984 | European Pat. Off. |
| 2369261 | 5/1978 | France |
| 1584202 | 2/1981 | United Kingdom |
| 1584203 | 2/1981 | United Kingdom |

OTHER PUBLICATIONS

S. M. Spatz et al., "Some N-substituted tetrabromophthalimide fire-retardant additives", Industrial and Engineering Chemistry Product Research and Development, vol. 8, No. 4 (1969) pp. 397–398.

Drew et al., "Chemiluminescent Organic Compounds. Part I. Isomeric Simple and Complex Hydrazides of Phthalic Acid and Mode of Formation of Phthalazine and iso Indole Rings" Queen Mary College (University of London) pp. 10–36 (1936).

Jones, "The Reaction of Hydrazine with Polyimides, and Its Utility", Journal of Polymer Science, No. 22, pp. 773–784 (1969).

Chemical Abstracts vol. 83, 180336j, p. 56, 1975.
Chemical Abstracts vol. 89, 164471t, p. 39, 1978.

Primary Examiner—Kriellion S. Morgan
Attorney, Agent, or Firm—Pennie & Edmonds

[57] ABSTRACT

The invention relates to the preparation of halogenated imides derived from hydrazine and halogenated dicarboxylic acid anhydride and which can be used as flame-proofing agents for plastics. The condensation of hydrazine and halogenated dicarboxylic acid anhydride is carried out in an aqueous medium, at a temperature ranging from 40° to 225° C., with a molar ratio of anhydride/hydrazine equal to between 0.5 and 3, preferably between 1 and 2.

14 Claims, No Drawings

PREPARATION OF FLAME-RESISTANT HALOGENATED IMIDES

This is a continuation-in-part, of application Ser. No. 011,099, filed Feb. 5, 1987, abandoned.

TECHNICAL FIELD

The present invention relates to the synthesis of polyhaloimides and, more particularly, to those imides derived from halogenated dicarboxylic acids such as tetrabromophthalic acid.

BACKGROUND ART

Polyhaloimides, especially tetrabromophthalimides and bis(tetrabromophthalimides), are well-known compounds which find an application as flame retardants in many inflammable substances, especially in plastics (see, for example, the articles by S. M. SPATZ et al. entitled "Some N-substituted tetrabromophthalimide fire-retardant additives" in Industrial and Engineering Chemistry Product Research and Development, vol. 8, No. 4 (1969) pages 397-398, as well as U.S. Pat. No. 3,873,567, French patent 2,369,261 and Japanese applications 74-045,062 and 75-064,337.

However, the preparation processes described in the references mentioned above give poor yields and provide products which are most frequently yellow in color or which become colored when they are used and thereby confer to plastics (compounds or molded articles) a color which is and unacceptable in a good many uses. Moreover, these products very often contain substances which are volatile at the temperatures at which they are used in some polymeric substances and lead to the corrosion of molds. Additionally, the use in their preparation of organic solvents (especially xylene, toluene, alcohol, acetic acid), most frequently chosen because of their capacity to form azeotropic mixtures with water which enable the water of condensation produced by the imidification reaction to be carried over or to dissolve the halogenated dicarboxylic acid anhydride, require expensive operations for the separation and the recovery of these solvents, as well as drying means suitable for the removal of the organic solvent vapors.

The disadvantages mentioned above are encountered especially in the case of polyhaloimides derived from hydrazine and halogenated dicarboxylic acid anhydrides. It has now been found that it is not indispensable to use an organic solvent to dissolve the anhydride and/or remove the water of condensation and that by operating in an aqueous medium under certain conditions, colorless or very slightly colored products which, without prior purification, are perfectly suitable for flameproofing macromolecular substances, including those which are employed at high temperature, especially above 250° C., may be obtained with very high yields and without effluent disposal and environmental problems.

DETAILED DESCRIPTION OF THE INVENTION

The process according to the invention which consists in condensing hydrazine with a halogenated dicarboxylic acid anhydride, is characterized in that the reaction is carried out in an aqueous medium, at a temperature ranging from 40° to 225° C., and with a molar ratio anhydride/hydrazine substantially equal between about 0.5 and 3, preferably 1 to 2, for a sufficient time to form the halogenated imide.

Among the halogenated anhydrides which can be used, the following may more particularly be mentioned:

anhydrides of aromatic dicarboxylic acids (benzene, naphthalene, anthracene), especially those of general formula:

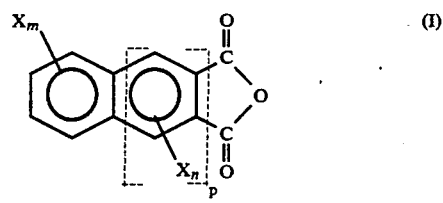

in which X represents a bromine or chlorine atom, m is an integer ranging from 2 to 4, n and p are integers ranging from 0 to 2;

anhydrides of alicyclic dicarboxylic acids, such as 1,4,5,6,7,7-hexabromobicyclo[2.2.1]hept-5-ene-2,3-dicarboxylic acid and its chlorinated analogs (chlorendic acid), corresponding to the formula:

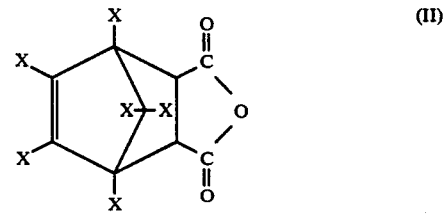

in which X has the same meaning as above. Bromophthalic anhydrides, for example 3,4- (or 3,6- or 4,5-)dibromophthalic anhydride, 3,4,6-tribromophthalic anhydride and more particularly tetrabromophthalic anhydride are preferably used.

According to the present invention, a single anhydride or a mixture of two or more anhydrides may be used. Commercial anhydrides which often contain a small quantity of inorganic acids may be used as such without prior purification. In fact, it has been observed that particularly good results are obtained when the solution or the aqueous dispersion containing the anhydride employed is acidic or strongly acidic (pH less than 7 or less than 4, respectively).

The quantity of water forming the reaction medium of the process according to the invention may vary within wide limits, the only condition being that it is adequate to ensure a satisfactory dispersion of the reagents and to allow a thorough agitation. This condition is generally achieved by using a quantity of water such that the solid matter content of the reaction medium is between approximately 5 and 75% by weight, and preferably between 20 and 40%.

The reaction may be carried out at atmospheric pressure at a temperature ranging from 40° to 100° C. or, subject to operating under pressure, at a higher temperature which can range up to 225° C. The reaction is preferably carried out between 100° and 225° C., which corresponds to pressures between approximately 1 and 25 bars.

Hydrazine in the form of its hydrate or a hydrazinium salt (for example sulphate, hydrohalide, acetate) may be used as such or in the form of dilute aqueous solution.

Hydrazine hydrate in the form of commercial aqueous solution is preferably used. The process according to the invention is advantageously carried out by introducing hydrazine gradually into the solution or dispersion of the halogenated anhydride which has been heated beforehand and maintained with stirring.

The reaction period may vary within wide limits, but is generally between 1 and 20 hours. After cooling the reaction medium, the solid suspension obtained is filtered and, if required, washed with water until the filtrate is neutral, the product is then dried by conventional drying means.

Various mole ratios of anhydride to hydrazine can be used depending upon the results desired. When the process according to the invention is carried out with a mole ratio of about 2 and at a temperature not less than 140° C., the product obtained generally consists of the bis(imide) corresponding to the following general structure:

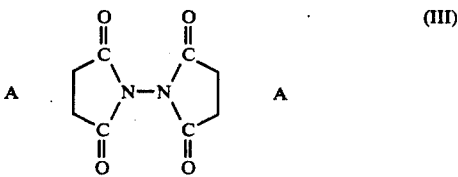

(III)

in which A represents the residue of the halogenated anhydride employed.

At lower temperatures, the product obtained contains, in addition to the bis(imide) of formula (III), a variable proportion, which may range from about 1 to 80% by weight, of a substantially equimolar mixture of the starting halogenated anhydride and the N-aminoimide corresponding to the general structure:

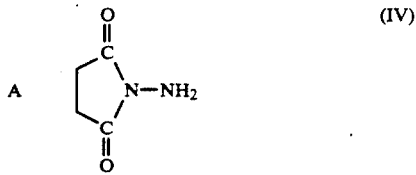

(IV)

in which A has the same meaning as above, it being possible for this N-aminoimide to be in the form of a salt, such as sulphate, hydrohalide, acetate, etc. The closer that the reaction temperature is to 140° C., the higher the bis(imide) (III) content in the obtained product.

When a ratio of about 1 or less is used, the product obtained is primarily the N-amino-imide of general structure (IV). When this product is desired, hydrazine should be used in an amount of between stoichiometric and a 50% molar excess, and preferably the anhydride/hydrazine ratio to be used should be substantially equal to 1.

If a mole ratio of anhydride/hydrazine of between 1 and 2 is used, a mixture of the above products is obtained, containing an amount of bis(imide) which increases proportionately as the ratio is closer to 2 and as the temperature is increased.

Irrespective of whether they are pure bis(imides), pure N-aminoimide or bis(imide), N-aminoimide, and anhydride mixtures, the products obtained in accordance with the the invention are particularly well suited as flame retardants in plastics of all kinds. Their incorporation into these substances may be carried out by any known method at doses ranging from 5 to 40% relative to the weight of the inflammable substance.

The following examples, in which the parts and the percentages are expressed on a weight basis, illustrate the invention without limiting it. The products obtained were identified by CHN and IR analyses and yield is expressed relative to the anhydride component.

EXAMPLE 1

1,114 parts of commercial grade tetrabromophthalic anhydride are dispersed in 3,000 parts of distilled water in a glass reactor equipped with a stirrer and a refluxing device. The pH of the suspension is 2.2.

After heating the suspension to 60° C., 60 parts of 100% hydrazine hydrate are added gradually in the course of 20 to 30 minutes, and the reaction mixture is then heated to 100° C. During the first seven hours of reaction at this temperature, the dispersion is yellow. 1,600 parts of distilled water are then added and the dispersion is maintained at 100° C. for a further period of 7 hours. A white to ivory-white suspension is then obtained, which is cooled and filtered through a Buchner funnel. After washing to a neutral pH with water and drying under vacuum at 110°-120° C., an ivory-white product is obtained with a yield greater than 96%. Analysis of the product shows that it contains approximately:

40% of N,N'-bis(tetrabromophthalimide)
30.5% of N-aminotetrabromophthalimide
29.5% of tetrabromophthalic anhydride.

These percentages were determined by successive extractions with solvents specific to tetrabromophthalic anhydride and to N-aminotetrabromophthalimide (methanol and dimethyl sulphoxide, respectively), N,N'-bis(tetrabromophthalimide) being insoluble in these solvents. Other identification methods (NMR and IR spectroscopy analyses, DTA and TGA thermal analyses) were also used for identifying the different compounds.

EXAMPLE 2

The reaction is carried out as in Example 1, but adding 2.5 parts of 96% sulphuric acid to the aqueous suspension of tetrabromophthalic anhydride. The pH is then 1.1.

An ivory-white product is obtained with a yield greater than 98%. The product contains approximately:
29% of N,N'-bis(tetrabromophthalimide)
36% of N-aminotetrabromophthalimide (partly in the form of sulphate), and
35% of tetrabromophthalic anhydride.

EXAMPLE 3

186 parts of commercial grade tetrabromophthalic anhydride are dispersed in 600 parts of distilled water heated to 115° C. with the aid of a heating jacket in a one-liter autoclave, equipped with a stirrer. The pH of the suspension is 2.2.

10 parts of 100% hydrazine hydrate diluted with 100 parts of distilled water are introduced gradually into the suspension, by means of a pump. At the beginning of the introduction, the pressure is approximately 3 bars; at the end of the introduction, the pressure is approximately 5 bars and the temperature 130° C.

These conditions (5 bars, 130° C.) are maintained for approximately 8 hours, the reaction mixture is then cooled by circulating cold water and the suspension obtained is filtered. After washing to neutral pH with water and drying 25 under vacuum at 100°–110° C., a white product is obtained with a yield of 97%. The product contains approximately:

95% of N,N'-bis(tetrabromophthalimide)
2.6% of N-aminotetrabromophthalimide, and
2.4% of tetrabromophthalic anhydride.

EXAMPLE 4

1,335 parts of commercial grade tetrabromophthalic anhydride are dispersed in 4,500 parts of distilled water, in a 6-liter autoclave equipped with a stirrer and a heating means (for example, jacket). The pH of the suspension is 2.2.

This suspension is heated to 150° C., 72 parts of hydrazine hydrate diluted in 125 parts of distilled water are then gradually introduced therein and the pressure is then maintained between 5 and 6 bars for approximately 5 hours.

The reaction mixture is then cooled by circulating cold water, and the suspension is then filtered. After washing to neutral pH with water and drying under vacuum at 100°–110° C., a white product consisting of practically pure N,N'-bis(tetrabromophthalimide) is obtained with a yield of 97%.

EXAMPLE 5

890 parts of chlorendic anhydride (anhydride of 1,4,5,6,7,7-hexachlorobicyclo[2.2.1]hept-5-ene-2,3-dicarboxylic acid) are dispersed in 3,000 parts of distilled water, in the same apparatus as in Example 1, and the mixture is heated to 60° C. The pH of the suspension is approximately 2.

60 parts of 100% hydrazine hydrate are then added gradually (in the course of 20 to 30 minutes), the suspension is then heated to 100° C. and maintained at this temperature for approximately 12 hours.

A part of the water is removed from the reaction mixture by distillation, until a wet paste is obtained, which is drained, and then washed to neutrality with cold water and dried in an oven under vacuum at 100° C. for 8 hours.

An ivory-white product is thereby obtained. The product contains approximately:

90% of N,N'-bis(chlorendimide)
5% of N-aminochlorendimide, and
5% of chlorendic anhydride.

EXAMPLE 6

800 parts of tetrachlorophthalic anhydride are dispersed in 10,000 parts of distilled water in the same apparatus as in Example 1.

The suspension, the pH of which is approximately 2, is then heated to 90° C. and 70 parts of 100% hydrazine hydrate are added in the course of approximately 2 hours. After approximately 12 hours of reaction at 98° C., the suspension is cooled, filtered and washed to neutral pH with water.

After drying under vacuum in an oven, a white product is obtained with a yield greater than 96%. The product consists of approximately:

68% of N,N'-bis(tetrachlorophthalimide)
16% of N-aminotetrachlorophthalimide, and
16% of tetrachlorophthalic anhydride.

EXAMPLE 7

372 parts of tetrachlorophthalic anhydride and 603 of tetrabromophthalic anhydride are dispersed in 4,000 parts of distilled water in the same apparatus as in Example 1.

The suspension thus obtained (pH approximately 2) is then heated to 90° C., 65 parts of 100% hydrazine hydrate are then added in the course of 3 to 4 hours and the reaction is allowed to proceed for 12 hours at 98° C.

After filtering, washing to neutral pH with water and drying under vacuum at 110°–120° C. for 8 hours, a white product is obtained with a yield greater than 96%. The product consists of approximately:

50% of a mixture of N,N'-bis(tetrachloro- and tetrabromophthalimides),
25% of a mixture of N-aminotetrachlorophthalimide and N-aminotetrabromophthalimide, and
25% of a mixture of tetrachloro- and tetrabromophthalic anhydrides.

EXAMPLE 8

153 parts of 1,4,5,6,7,7-hexabromobicyclo[2.2.1]-hept-5-ene-2,3-dicarboxylic anhydride, hereinafter called "bromendic anhydride" and prepared from hexabromocyclopentadiene and maleic anhydride are dispersed in 500 parts of distilled water in an apparatus similar to that in Example 1. The pH of the suspension is approximately 2.3.

The mixture is heated to 97° C., 6 parts of 100% hydrazine hydrate are then added gradually (in the course of 20 to 30 minutes) and the mixture is then maintained at 100° C. for 12 hours.

A part of the water is removed by distillation until a wet paste is obtained, which is drained, and then washed to neutral pH with water and dried in an oven under vacuum at 100°–110° C. for 8 hours. A slightly colored product is thereby obtained. The product consists of approximately:

65% of N,N'-bis(bromendimide)
17.5% of N-aminobromendimide, and
17.5% of bromendic anhydride.

EXAMPLE 9 (comparative)

619 parts of tetrabromophthalic anhydride are dissolved at 66° C. in 1,500 parts of methanol in an apparatus similar to that in Example 1. After complete dissolution, 34 parts of 100% hydrazine hydrate are added, and the solution is maintained at 67° C. for approximately 8 hours.

After cooling, filtering and washing with methanol followed by water, a yellow product, which does not contain tetrabromophthalic anhydride and mainly consists of N-aminotetrabromophthalimide with a small amount of N,N'-bis(tetrabromophthalimide) and other unidentified products, is obtained with a yield of approximately 75%.

EXAMPLE 10 (comparative)

619 parts of tetrabromophthalic anhydride are introduced into 750 parts of dimethylformamide and 1,250 parts of xylene in an apparatus similar to that in Example 1, the mixture is then heated to 100° C. A yellow solution is then obtained, to which 34 parts of 100% hydrazine hydrate are added. The mixture is then heated to 138° C. and maintained at this temperature for approximately 8 hours, while removing the water formed by azeotropic distillation with xylene.

After cooling, filtering, washing with hexane and drying under vacuum, a yellow product, which does not contain tetrabromophthalic anhydride and mainly consists of N,N'-bis(tetrabromophthalimide) with a small amount of N-aminotetrabromophthalimide and other unidentified products, is obtained with a yield of approximately 78%.

EXAMPLE 11

429 parts of commercial grade tetrachlorophthalic anhydride are dispersed in 2,000 parts of distilled water in a glass reactor equipped with a stirrer and a refluxing device. The pH of the suspension is 1.5.

After heating the suspension to 60° C., 75 parts of 100% hydrazine hydrate are added gradually in the course of 20 to 30 minutes, and the reaction mixture is then heated to 100° C. 1,000 parts of distilled water are then added and the mixture is maintained at 100° C. for a further period of 10 hours. A suspension is then obtained, which is cooled and filtered through a Buchner funnel. After washing to a neutral pH the residue is washed with water and drying under vacuum at 110°-120° C., a white product is obtained with a yield greater then 97%. Elemental and IR analyses of the product confirms the structure:

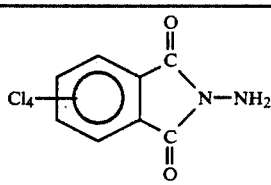

| | CHN elemental analysis | |
|---|---|---|
| | Found | Theory |
| C % | 32.3 | 32.5 |
| H % | 0.7 | 0.7 |
| N % | 9.0 | 9.5 |

EXAMPLE 12

Using the same procedure as in Example 11, 445 parts of commercial chlorendic anhydride are dispersed in 4,000 parts of water. The pH of the suspension is 2.5.

60 g of 100% hydrazine hydrate are gradually added to the suspension, which is heated to 98° C. After 10 hours reaction at this temperature, the mixture is cooled and the product separated by filtration.

After the residue is washed to a neutral pH and dried under vacuum at 110°-120° C., a grey product is obtained in a yield of greater than 90%. Elemental and IR analysis of this product confirms the structure:

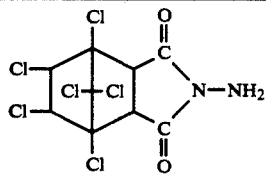

| | CHN elemental analysis | |
|---|---|---|
| | Measured | Theoretical |
| C % | 27.9 | 28.1 |
| H % | 1.7 | 1.1 |
| N % | 7.3 | 7.3 |

EXAMPLE 13

1,392 parts of tetrabromophthalic anhydride are dispersed in 4,000 parts of water is a six-liter autoclave which is equipped with a stirrer. The pH of the dispersion is 1.5.

The mixture is heated to 60° C. and 225 parts of 100% hydrazine hydrate are then added gradually. The suspension is then heated to 125° C. under pressure and maintained for 10 hours. After this reaction time, the mixture is cooled and the product separated by filtration.

After the residue is washed to a neutral pH and dried under vacuum at 110°-120° C., a yellow product is obtained in a yield of greater than 90%. Elemental and IR analysis of this product indicates the structure:

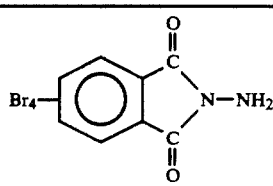

| | CHN analysis | |
|---|---|---|
| | Found | Theoretical |
| % C | 19.58 | 20.1 |
| % H | 0.32 | 0.4 |
| % N | 5.68 | 5.9 |

EXAMPLE 14

The procedure of Example 13 is repeated, except that a 100% molar excess of hydrazine hydrate is used. The same product is obtained as in Example 13, in a 97.4% yield.

EXAMPLE 15

883 parts of commercial tetrabromophthalic anhydride are dispersed in 2,600 parts of distilled water in a four liter autoclave equipped with a stirrer. This mixture is heated with stirring to a temperature of 170° C., which corresponds to a pressure of between 7.6 and 8 bars.

53 parts of 100% hydrazine hydrate, diluted with 200 parts of distilled water (a mole ratio TBPA/HH of 1.8), are introduced gradually into the stirred suspension by means of a pump.

The reaction medium is maintained at 170° C. for 6 hours, then cooled and filtered, and the product washed. After drying at 100°-110° C. under vacuum, a white product is obtained in a 95% yield, containing:
  83% of N,N'-bis(tetrabromophthalimide)
  14% of N-aminotetrabromophthalimide
  3% of tetrabromophthalic anhydride.

EXAMPLE 16

The efficacy of the products according to the invention as flameproofing agents for plastics was tested according to the following general procedure:

The resin in the form of a powder or in the form of granules are mixed with the flameproofing agent to be tested and the optional additives (antimony trioxide, paraffin) in the proportions given in the following tables, using a planetary or "barrel" type of mixer. After homogenization, the mixture is extruded by means of a suitable extruder (twin screw, single screw or "Buss" type), equipped or otherwise with a degassing means, operating at the extrusion temperature recommended by the supplier of the resin and related to the melting point of the polymer. The compound obtained, granulated if required, is then converted into test-pieces by means of an injection molding machine operating at suitable temperatures. These test-pieces are ten subjected to standard tests for flameproofing (i.e., UL94) at 3.2 mm and 1.6 mm (French Standard NF T51,072) and for oxygen index OI% (French Standard NF T51,071).

Table A and C summarizes the results obtained in the case of polybutylene terephthalate (TMNO-ORGATER, granules marketed by Atochem).

Table B collates the results obtained with the product of Example 1 and other resins, viz.:

polypropylene (PK-1060 P, marketed by Hoechst in the form of a powder), polyamide 12 (AMNO-RILSAN, marketed by Atochem in the form of granules), ABS resin (UGIKRAL SF, marketed by CdF-Chimie in the form of a powder).

While it is apparent that the invention herein disclosed is well calculated to fulfill the desired results, it will be appreciated that numerous modifications and embodiments may be devised by those skilled in the art, and it is intended that the appended claims cover all such modifications and embodiments as fall within the true scope of the present invention.

3. The process according to claim 1, in which the pH of the aqueous solution of anhydride used as the starting material is less than 4.

4. The process according to claim 1, in which one of the anhydrides of the following formula or mixtures thereof is used as a reactant:

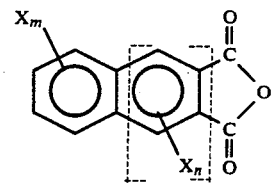

or

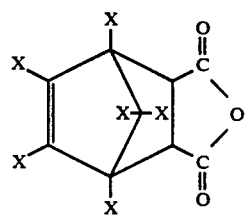

in which X represents a bromine or chlorine atom, m is an integer ranging from 2 to 4, n and p are integers ranging from 0 to 2.

5. The process according to claim 4, in which tetrabromophthalic anhydride, tetrachlorophthalic anhydride, chlorendic anhydride, bromendic anhydride or mixtures thereof are used as a reactant.

6. The process according to claim 1, in which hydrazine is used in the form of a hydrate or hydrazinium salt.

TABLE A

| | TRIAL No. | | | | | | | |
|---|---|---|---|---|---|---|---|---|
| | I control | II | III | IV | V | VI | VII | VIII (comparative) |
| Flameproofing agent of Example No. | None | 1 | 4 | 5 | 6 | 7 | 9 | 10 |
| Composition (parts by weight): | | | | | | | | |
| TMNO-ORGATER resin | 1000 | 790 | 3160 | 3449 | 3402 | 3290 | 1559 | 1559 |
| Flameproofing agent | 0 | 126 | 588 | 308 | 355 | 467 | 290 | 290 |
| Antimony trioxide | 0 | 60 | 246 | 243 | 243 | 243 | 121 | 121 |
| Paraffin | 0 | 15 | 60 | 60 | 60 | 60 | 30 | 30 |
| Results of tests: | | | | | | | | |
| UL94 | NC | V0 | V0 | V2 | V2 | V0 | V0 | V0 |
| OI % | 22 | 32.6 | 31.3 | 25.1 | 23.7 | 27.6 | 30.1 | 31.7 |
| Colour of the, test-piece: | white | ivory-white | white | slightly grey | ivory-white | ivory-white | yellow | yellow |

TABLE B

| | Composition (parts by weight) | | | Results of tests | | Colour of the |
|---|---|---|---|---|---|---|
| RESIN | Resin | Flameproofing agent of Example 1 | Antimony trioxide | UL94 | OI % | test-piece |
| PK 1060 P | 1000 (control) | 0 | 0 | NC | 18 | white |
| " | 522 | 359 | 119 | V0 | 25 | ivory-white |
| AMNO-RILSAN | 1000 (control) | 0 | 0 | V2 (at 3.2 mm) | 22 | slightly yellow |
| " | 877 | 96 | 26 | V0 | 29.4 | pale yellow |
| UGIKRAL SF | 1000 (control) | 0 | 0 | NC | 18 | beige |
| " | 766 | 150 | 50 | V0 (at 3.2 mm) | 25.6 | light beige |

What is claimed is:

1. A process for the preparation of halogenated imides which comprises reacting hydrazine and a halogenated dicarboxylic acid anhydride in an acidic aqueous medium, at a temperature ranging from 40° to 225° C. and with a molar ratio of anhydride/hydrazine equal to between about 1 and 3 for a sufficient time to form a mixture of halogenated bis(imides) and N-aminoimides.

2. The process according to claim 1, in which the reaction is carried out under pressure at a temperature of at least 140° C.

7. The process of claim 1 wherein the solids content of the reaction medium ranges from about 5 to 75% by weight.

8. A process for the preparation of halogenated imides which comprises reacting hydrazine in the form of a hydrate or hydrazinium salt in a dilute acidic aqueous solution with a solution of a halogenated dicarboxylic acid anhydride at a temperature of between 100° and 225° C. with a molar ratio of anhydride/hydrazine of between about 1 and 2 and wherein the solids content of the reaction medium ranges between 5 and 75% by weight, for a sufficient time to form a mixture of halogenated bis(imides) and N-aminoimides.

9. A process for the preparation of halogenated imides which comprises reacting hydrazine in the form of a hydrate or hydrazinium salt in a dilute aqueous solution with a halogenated dicarboxylic acid anhydride of the formula:

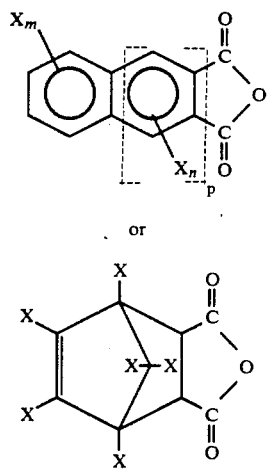

or

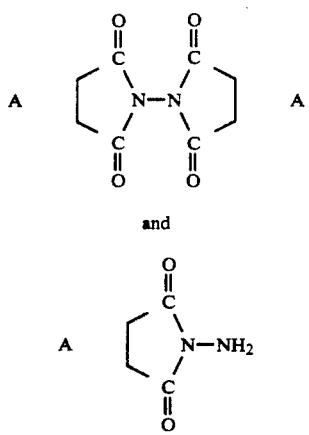

at a temperature of between 100° and 225° C. with a molar ratio of anhydride/hydrazine of between about 0.5 and 2 and wherein the solution has a pH of less than about 4 and the solids content of the reaction medium ranges between 5 and 75% by weight, for a sufficient time to form a mixture of halogenated bis(imides) and N-aminoimides of the formulae:

$$A \left[ \begin{array}{c} O \\ \parallel \\ C \\ \diagup \\ N-N \\ \diagdown \\ C \\ \parallel \\ O \end{array} \right] A$$

and $$A \left[ \begin{array}{c} O \\ \parallel \\ C \\ \diagup \\ N-NH_2 \\ \diagdown \\ C \\ \parallel \\ O \end{array} \right]$$

in which X represents a bromine or chlorine atom, m is an integer ranging from 2 to 4, n and p are integers ranging from 0 to 2.

10. The process according to claim 9, in which tetrabromophthalic anhydride, tetrachlorophthalic anhydride, chlorendic anhydride, bromendic anhydride or mixtures thereof are used as the anhydride.

11. The process according to claim 9, in which the reaction is carried out under pressure at a temperature of at least 140° C. and at a molar ratio near 2 to increase the bis(imide) content of the mixture.

12. A process for the preparation of halogenated imides which comprises reacting hydrazine in the form of a hydrate or hydrazinium salt in a dilute aqueous solution with a halogenated dicarboxylic acid anhydride of the formula:

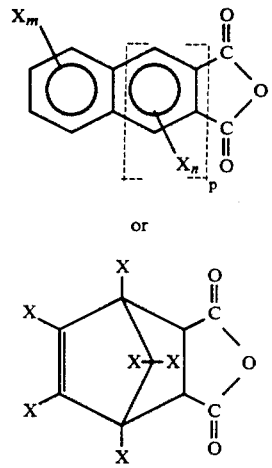

or

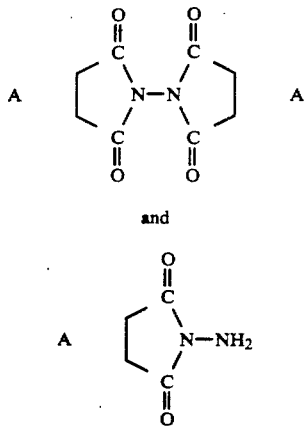

at a temperature of between 100° and 225° C. with a molar ratio of anhydride/hydrazine of between about 0.5 and 2 and wherein the solution has a pH of less than about 7 and the solids content of the reaction medium ranges between 5 and 75% by weight, for a sufficient time to form a mixture of halogenated bis(imides) and N-aminoimides of the formulae:

$$A \left[ \begin{array}{c} O \quad O \\ \parallel \quad \parallel \\ C \quad C \\ \diagup \quad \diagdown \\ N-N \\ \diagdown \quad \diagup \\ C \quad C \\ \parallel \quad \parallel \\ O \quad O \end{array} \right] A$$

and $$A \left[ \begin{array}{c} O \\ \parallel \\ C \\ \diagup \\ N-NH_2 \\ \diagdown \\ C \\ \parallel \\ O \end{array} \right]$$

in which X represents a bromine or chlorine atom, m is an integer ranging from 2 to 4, n and p are integers ranging from 0 to 2.

13. The process according to claim 12, in which tetrabromophthalic anhydride, tetrachlorophthalic anhydride, chlorendic anhydride, bromendic anhydride or mixtures thereof are used as the anhydride.

14. The process according to claim 12, in which the reaction is carried out under pressure at a temperature of at least 140° C. and at a molar ratio near 1 to increase the N-aminoimide content of the mixture.

* * * * *

UNITED STATES PATENT AND TRADEMARK OFFICE
CERTIFICATE OF CORRECTION

PATENT NO. : 5,137,948

DATED : August 11, 1992

INVENTOR(S) : Evelyne Bonnet; Andre Gagnieur; Bernard Gurtner

It is certified that error appears in the above-identified patent and that said Letters Patent is hereby corrected as shown below:

Title page,
Under Item [30] "Foreign Application Priority Data",

Feb. 12, 1987 should read Feb. 12, 1986.

Title page,
Under Item [56] "References Cited", U.S. PATENT DOCUMENTS, add the following references:

| | | | |
|---|---|---|---|
| 3,959,219 | 5/1976  | Aoyama et al. | 260/45.75 B |
| 4,003,862 | 1/1977  | Albright      | 160/2.5 AJ  |
| 4,254,011 | 3/1981  | Bier          | 260/40 R    |
| 4,284,550 | 8/1981  | Mizuno et al. | 260/40      |
| 4,477,523 | 10/1984 | Biggs et al.  | 428/389     |

Signed and Sealed this

Ninth Day of November, 1993

Attest:

BRUCE LEHMAN

*Attesting Officer*      *Commissioner of Patents and Trademarks*